United States Patent [19]
Kirstein et al.

[11] Patent Number: 5,945,433
[45] Date of Patent: Aug. 31, 1999

[54] QUINOLINE DERIVATIVES CONTAINING A DIOL AS LEUKOTRIENE ANTAGONISTS

[75] Inventors: Dorte Kirstein, Lyngby; Schneur Rachlin, Hørsholm, both of Denmark

[73] Assignee: Leo Pharmaceutical Products, Ltd. A/S, Ballerup, Denmark

[21] Appl. No.: 08/983,452

[22] PCT Filed: Nov. 13, 1996

[86] PCT No.: PCT/DK96/00467

§ 371 Date: Jan. 13, 1998

§ 102(e) Date: Jan. 13, 1998

[87] PCT Pub. No.: WO97/19925

PCT Pub. Date: Jun. 5, 1997

[30] Foreign Application Priority Data

Nov. 27, 1995 [GB] United Kingdom .................. 9524185

[51] Int. Cl.⁶ .................. C07D 215/12; A61K 31/47
[52] U.S. Cl. ........................... 514/311; 546/176
[58] Field of Search ............... 514/311; 546/176

[56] References Cited

FOREIGN PATENT DOCUMENTS

94/03431   2/1994   WIPO .

OTHER PUBLICATIONS

Lewis et al, New Eng. J. Med., 323 (1990), pp. 645–655.
Goetzl et al, J. Clin. Immunol., 4 (1984), pp. 79–84.

*Primary Examiner*—D. Margaret M. Mach
*Attorney, Agent, or Firm*—Pillsbury Madison & Sutro, LLP

[57] ABSTRACT

The present invention relates to hitherto unknown compounds of formula (I) in which $R_1$ is hydrogen or halogen, preferably fluorine or chlorine, and m is 0, 1 or 2. The present compounds are of value in the human and veterinary practice as leukotriene antagonists.

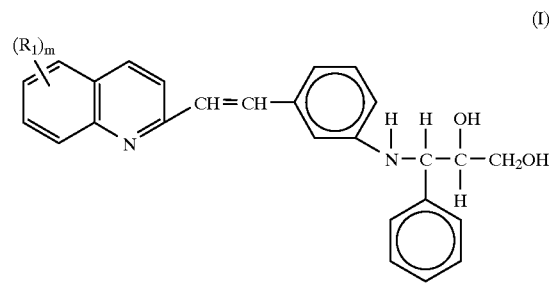

9 Claims, No Drawings

QUINOLINE DERIVATIVES CONTAINING A DIOL AS LEUKOTRIENE ANTAGONISTS

The present invention relates to hitherto unknown compounds useful in the human and veterinary therapy, to pharmaceutically acceptable salts thereof, to bioreversible derivatives thereof, to methods for producing said new compounds, to pharmaceutical compositions containing the new compounds, to dosage units of the compositions, and to methods of treating patients using said compositions and dosage units.

Leukotrienes, which are formed via the 5-lipoxygenase pathway of arachidonic acid metabolism, are implicated in a variety of pathophysiologic functions, such as bronchoconstriction, plasma exudation, coronary artery spasm, leukocyte chemotaxis and neutrophil degranulation[1]. It is therefore of considerable interest to develop compounds which antagonize the effects of leukotrienes.

[1] R. A. Lewis, K. F. Austen and R. J. Soberman, New Eng. J. Med. 323 (1990) 645.

International patent application No. PCT/DK93/00254 (Publication No. WO94/03431) describes a series of quinolyl substituted N-phenyl substituted isoserines with leukotriene antagonistic activity.

Now we have surprisingly found that novel diol containing compounds according to general formula I are very potent antagonists, especially in the presence of human serum albumin, and with superior bioavailability and prolonged activity in vivo.

The present compounds have the general formula I

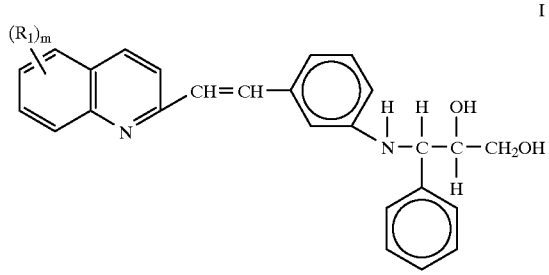

$R_1$ is hydrogen or halogen, preferably fluorine or chlorine, and m is 0, 1 or 2;

The compounds described herein contain more centres of asymmetry and may thus give rise to stereoisomers. The present invention is meant to comprise all such possible stereoisomers as well as their racemic and stereo-chemical mixtures.

The present salts of the compounds of formula I may be formed with pharmaceutically acceptable inorganic or organic acids, such as hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid.

5-Lipoxygenase inhibitors and leukotriene antagonists are of potential interest in the therapy of asthma, allergy, rheumatoid arthritis, spondylo-arthritis, gout, atherosclerosis, proliferative and inflammatory skin disorders, such as psoriasis and atopic dermatitis, chronic inflammatory bowel disease, and other inflammatory conditions, vasospasm associated with angina pectoris, pulmonary hypertension, cystic fibrosis, the adult respiratory distress syndrome, ischemic and reperfusion injury, migraine headache, etc.[2]. The identification of specific 5-lipoxygenase inhibitors and leukotriene antagonists is thus a novel approach with very wide implications for the treatment of a diversity of clinical disorders.

[2] E. J. Goetzl, D. G. Payan and D. W. Godman, J. Clin. Immnol. 4 (1984) 79.

Leukotriene antagonists may be identified by observing the contractions elicited in preparations of guinea-pig ileum strips suspended in a physiological buffer by addition of pure leukotriene $D_4$ ($LTD_4$)[3]. When the compounds of the present invention were added to the ileum preparation before addition of $LTD_4$ a significant inhibition occurred of the specific $LTD_4$- induced contraction. This inhibition occurred at concentrations as low as 0.1–1 nM. On the other hand, contractions induced with histamine at $10^{-7}$ M were not inhibited by these compounds even at micromolar concentrations.

[3] I. Ahnfelt-Rønne, D. Kirstein and C. Kærgaard-Nielsen, European J. Pharmacol. 155 (1988) 1–17.

It is of importance to investigate the receptor binding properties of leukotriene antagonists in relation to their inhibition of smooth muscle contraction. Receptor binding studies may be performed with guinea-pig lung membranes in a direct competition assay between a leukotrien antagonist and $[^3H]LTD_4$ for binding to the $LTD_4$ receptor[3,4]. A $pIC_{50}$ value is determined as the negative logarithm of the molar concentration of antagonist inhibiting $[^3H]LTD_4$ binding by 50%. The $pIC_{50}$ values for the compounds of the present invention are equal to or higher than those for the reference compound SR3040[5] (see Table I)

[4] S. Mong, H.-L. Wu, M. O. Scott, M. A. Lewis, M. A. Clarke, B. M. Weichman, C. M. Kinzig, J. G. Gleason and S. T. Crooke, J. Pharmacol. Exp. Ther. 234 (1985) 316.
[5] International Patent Appl. No. PCT/DK93/00254 (Publ. No. WO 94/03431), Example 18.

TABLE I

Binding of $[^3H]LTD_4$ to guinea-pig lung membranes in the absence or presence of 0.1% human serum albumin ($pIC_{50}$– mean ± SD (n) or individual values)

| Compound | Absence of albumin | Presence of albumin |
| --- | --- | --- |
| Example 7 | 8.8 ± 0.1 (3) | 9.1 ± 0.1 (3) |
| Example 8 | 9.0 ± 0.3 (3) | 9.3 ± 0.2 (3) |
| Example 5 | 8.4 ± 0.1 (3) | 8.6 ± 0.1 (3) |
| Example 6 | 8.8 ± 0.5 (3) | 8.8 ± 0.4 (3) |
| Example 3 | 8.3 – 8.2 | 8.4 – 8.6 |
| Example 4 | 8.4 – 8.4 | 8.9 – 8.7 |
| SR3040 [5] | 8.9 ± 0.3 (3) | 8.8 ± 0.1 (3) |

The leukotriene antagonistic effect was tested in vivo on $LTD_4$-induced bronchoconstriction in anaesthetized guinea-pigs[3]. Intravenously the compounds were administered 10 minutes, orally 24, 48 and 72 hours before the bronchoconstriction. The $ED_{50}$ values represent the dose inhibiting the leukotriene induced bronchoconstriction by 50%. The $ED_{50}$ values were calculated by regression analysis of 2–3 doses. The following Table II shows the results.

TABLE II

| Compound | $ED_{50}$ mg/kg i.v. 10 min | $ED_{50}$ mg/kg p.o. 4 h | $ED_{50}$ mg/kg p.o 24 h | $ED_{50}$ mg/kg p.o 48 h | $ED_{50}$ mg/kg p.o 72 h |
|---|---|---|---|---|---|
| Example 7 | 0.058 | 1.64 | 4.64 | 9.73 | >30 |
| Example 8 | 0.18 | nd | 14.93 | >30 | nd |
| Example 3 | 0.30 | 0.956 | 20.32 | nd | nd |
| Example 4 | 0.35 | 3.63 | 8.66 | >30 | nd |
| SR3040[5] | 0.008 | 18.07 | >30 | nd | nd | nd = not done
The compounds of the present invention are superior to SR3040.

The present invention also relates to a method for producing the present compounds.

In one embodiment, an amine of the formula II

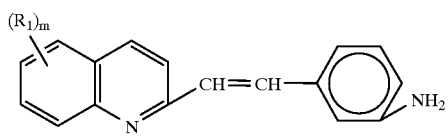

in which $R_1$ and m have the above meanings, is reacted with a compound of the formula III

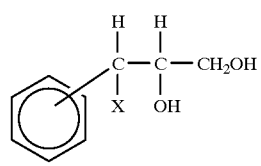

in which X is capable of forming a "good leaving group", X thus standing for e.g. a halogen atom, such, as chlorine, bromine or iodine, or an alkyl- or arylsulphonyloxy group, but other leaving groups can be used as well, such as an alkylsulphate group, a chlorosulphonyloxy group, an alkylsulphite group, a mono- or dialkylphosphate group or a nitrate group, to form a compound of the formula I.

The reaction is performed in a suitable inert organic solvent, such as dimethylformamid, but other solvents can be used as well. The reaction is preferably performed at ambient temperature, but in some cases it is convenient to cool the reaction mixture below room temperature, or to heat the reaction mixture above room temperature, up to the boiling point of the solvent used, depending on the nature of the reactants of the formulae II and III used. The crude reaction products of the formula I are collected by filtration, or, after dilution with water, extracted from the reaction mixture with a suitable solvent, such as diethyl ether, ethyl acetate, dichloromethane or chloroform. The products are purified e.g. by recrystallization or by chromatography.

In another embodiment, an amine of the formula II is reacted with a compound of the formula IV

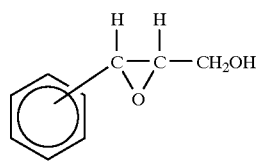

The reaction is performed either in a suitable inert organic solvent, such as methanol, ethanol, dimethylformamide or hexamethyl phosphoric triamide, or in water, or in mixtures thereof. The reaction is performed at a temperature about or above room temperature, up to the boiling point of the solvent used. In some cases it can, however, be convenient to cool the reaction mixture below room temperature, depending on the nature of the compound of the formula IV used. The isolation and purification of the products can be performed as described above.

The present compounds are intended for use in pharmaceutical compositions which are useful in the treatment of the above mentioned diseases.

The amount required of a compound of formula I (hereinafter referred to as the active ingredient) for therapeutic effect will, of course, vary both with the particular compound, the route of administration and the mammal under treatment. A suitable dose of a compound of formula I for systemic treatment is 0.1 to 20 mg per kilogram bodyweight, the most preferred dosage being 0.2 to 10 mg/kg of mammal bodyweight, administered one or more times daily.

In spray formulations, a suitable anti-asthmatic dose of a compound of formula (I) is 1 µg to 5 mg of compound per kilogram bodyweight, the most preferred dosage being 1 µg to 1 mg/kg of mammal bodyweight, for example from 1 µg to 0.5 mg/kg.

While it is possible for an active ingredient to be administered alone as the raw chemical, it is preferable to present it as a pharmaceutical formulation. Conveniently, the active ingredient comprises from 0.1% to 100% by weight of the formulation. Conveniently, dosage units of a formulation contain between 0.07 mg and 1 g of the active ingredient. For topical administration, the active ingredient preferably comprises from 1% to 2% by weight of the formulation but the active ingredient may comprise as much as 10% w/w. Formulations suitable for nasal or buccal administration may comprise 0.1 to 20% w/w, for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient (s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier, or in the form of an enema.

Formulations suitable for parenteral administration conveniently comprise a sterile oily or aqueous preparation of the active ingredient which is preferably isotonic with the blood of the recipient.

Formulations suitable for intra-articular or ophthalmic administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical or ophthalmic administration include liquid or semi-liquid preparations, such as oil-in-water or water-in-oil emulsions, ointments or pastes; or solutions or suspensions, such as drops.

Formulations suitable for administration to the nose or buccal cavity include powder, self-propelling and spray formulations, such as aerosols and atomizers.

Other formulations suitable for nasal administration include a fine powder which is administered in the manner in which snuff is taken, i.e. by rapid inhalation through the nasal passage from a container of the powder held close up to the nose.

In addition to the aforementioned ingredients, the formulations of this invention may include one or more additional ingredients.

The compositions may further contain other therapeutically active compounds usually applied in the treatment of the above mentioned pathological conditions, for instance glucocorticoids, anti-histamines, platelet activating factor (PAF) antagonists, anticholinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

The invention will now be further described in the following Examples:

EXAMPLE 1

(+)-2R,3R-E-3-N-[3-2-(quinolin-2-yl)ethenyl]-phenylamino-3-phenyl-1,2-propandiol A mixture of E-3-[2-(quinolin-2-yl)ethenyl]aniline (0.5 g, 2 mmol) (confer EP 0 206 751 A Merck Frosst Canada Inc) and (2R,3R-(+)-3-phenyl-glycidol (Aldrich) (0.3 g, 2 mmol) in ethanol (10 ml) is refluxed for 8 days. After cooling, the resulting precipitate is collected by filtration, and washed with ethanol and ether. The title compound is obtained with a melting point of 164–166° C. and $[\alpha]_D^{20}=+60.9°$ (c=1,0, $CH_3OH$).

EXAMPLES 2–8

By following the procedure of Example 1 and using the appropriate starting materials, compounds of Table III are obtained.

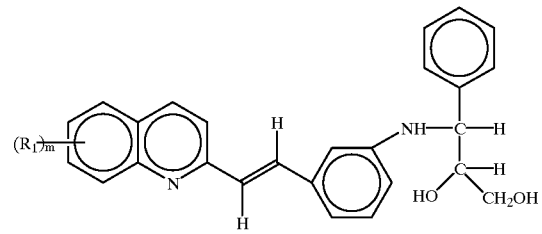

TABLE III

| Ex. No. | $(R_1)_m$ | Melting point (°C.) | Configuration $[\alpha]_D$ |
|---|---|---|---|
| 2 | H | 164–66 | 2S,3S –58.0° C. = 1, MeOH |
| 3 | 7—Cl | 185–86 | 2R,3R +59.5° C. = 1, MeOH |
| 4 | 7—Cl | 189–91 | 2S,3S –58.3° C. = 1, MeOH |
| 5 | 7—F | 172–74 | 2R,3R +57.5° C. = 1, MeOH |
| 6 | 7—F | 173–75 | 2S,3S –58.1° C. = 1, MeOH |
| 7 | 6—F,7—F | 162–64 | 2R,3R, +64.2° C. = 1, MeOH |
| 8 | 6—F,7—F | 162–64 | 2S,3S, –63.0° C. = 1, MeOH |

EXAMPLE 9

| Tablet | |
|---|---|
| (+)-2R,3R-E-3-N-[3-2-(6,7-difluoroquinolin-2--yl)ethenyl]-phenylamino-3-phenyl-1,2-propandiol (active substance) | 100 mg |
| Lactose | 75 mg |
| Starch | 12 mg |
| Methyl cellulose | 2 mg |
| Sodium carboxymethyl cellulose (CMC—Na) | 10 mg |
| Magnesium stearate | 1 mg |

The active substance, lactose and starch are mixed to a homogeneous state in a suitable mixer and moistened with a 5 percent aqueous solution of methylcellulose 15 cps. The mixing is continued until granules are formed. If necessary, the wet granulation is passed through a suitable screen and dried to a water content of less than 1% in a suitable dryer, e.g. fluid bed or drying oven. The dried granulaton is passed through a 1 mm screen and mixed to a homogeneous state with CMC—Na. Magnesium stearate is added, and the mixing is continued for a short period of time.

Tablets with a weight of 200 mg are produced from the granulation by means of a suitable tabletting machine.

What we claim is:

1. A compound of the formula I

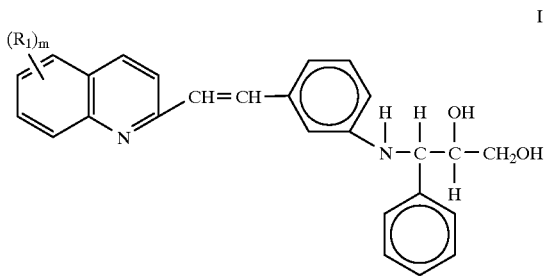

in which $R_1$ is hydrogen or halogen, and m is 0, 1 or 2; or pharmaceutically acceptable, non-toxic salt thereof.

2. A compound according to formula I of claim 1, in which $R^1$ is fluorine or chlorine.

3. A stereoisomer of a compound according to any one of claims 1–2, in pure form; or a mixture of such stereoisomers.

4. A salt according to claim 1 in which the salt is selected from the group consisting of salts formed with hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid.

5. A compound of claim 1 which is selected from the group consisting of:

(+)-2R,3R-E-3-N-[3-2-(6,7-difluoroquinolin-2-yl) ethenyl]-phenylamino-3-phenyl-1,2-propandiol, (+)-2R,3R-E-3-N-[3-2-(quinolin-2-yl)ethenyl]-phenylamino-3-phenyl-1,2-propandiol, (−)-2S,3S-E-3-N-[3-(2-quinolin-2-yl)ethenyl]-phenylamino-3-phenyl-1,2-propandiol, (+)-2R,3R-E-3-N-[3-2-(7-chloroquinolin-2-yl)ethenyl]-phenylamino-3-phenyl-1,2-propandiol, (−)-2S,3S-E-3-N-[3-2-(7-chloroquinolin-2-yl)ethenyl]-phenylamino-3-phenyl-1,2-propandiol, (+)-2R,3R-E-3-N-[3-2-(7-fluoroquinolin-2-yl)ethenyl]-phenylamino-3-phenyl-1,2-propandiol, (−)-2S,3S-E-3-N-[3-2-(7-fluoroquinolin-2-yl)ethenyl]-phenylamino-3-phenyl-1,2-propandiol, (−)-2S,3S-E-3-N-[3-2-(6,7-difluoroquinolin-2-yl) ethenyl]-phenylamino-3-phenyl-1,2-propandiol, or their salt or pure enantiomeric form.

6. A pharmaceutical preparation, containing a compound according to claim 1 together with a pharmaceutically acceptable carrier therefor.

7. A method of obtaining a leukotriene antagonistic activity in a patient in need of such treatment which comprises administering to said patient an effective amount of at least one compound according to claim 1.

8. A method according to claim 7 for the treatment and prophylaxis of a disease state selected from the group consisting of asthma, allergy, rheumatoid arthritis, spondyloarthritis, gout, atherosclerosis, proliferative and inflammatory skin disorders caused by leukotriene activity, chronic inflammatory bowel disease, vasospasm associated with angina pectoris, pulmonary hypertension, cystic fibrosis, the adult respiratory distress syndrome, ischemic and reperfusion injury, migraine headache.

9. Method for producing a compound of formula I according to claim 1, in which a) an amine of the formula II

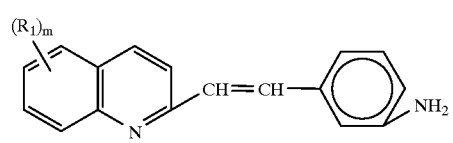

in which $R_1$ and m have the above meanings, is reacted with a compound of the formula III

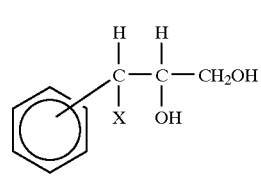

in which X is capable of forming a "good leaving group"; or b) an amine of the formula II is reacted with a compound of the formula IV

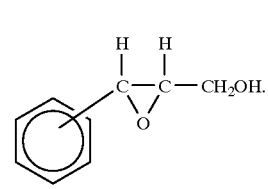

* * * * *